United States Patent
Suzuki et al.

(10) Patent No.: US 8,469,889 B2
(45) Date of Patent: Jun. 25, 2013

(54) ULTRASONOGRAPH THAT CHOOSES TRACKING WAVEFORMS FOR ATTRIBUTE VALUE CALCULATIONS

(75) Inventors: Takao Suzuki, Kanagawa (JP); Takenori Fukumoto, Kanagawa (JP)

(73) Assignee: Panasonic Corporation, Osaka (JP)

( * ) Notice: Subject to any disclaimer, the term of this patent is extended or adjusted under 35 U.S.C. 154(b) by 203 days.

(21) Appl. No.: 12/933,129

(22) PCT Filed: Jul. 30, 2008

(86) PCT No.: PCT/JP2008/002044
§ 371 (c)(1),
(2), (4) Date: Sep. 17, 2010

(87) PCT Pub. No.: WO2009/118798
PCT Pub. Date: Jan. 10, 2009

(65) Prior Publication Data
US 2011/0015524 A1 Jan. 20, 2011

(51) Int. Cl.
*A61B 8/00* (2006.01)
(52) U.S. Cl.
USPC ............ 600/437; 600/407; 600/438; 600/443
(58) Field of Classification Search
USPC .................................. 600/407, 437, 438, 443
See application file for complete search history.

(56) References Cited

U.S. PATENT DOCUMENTS

| | | | |
|---|---|---|---|
| 5,840,028 A | 11/1998 | Chubachi et al. | |
| 6,979,294 B1 * | 12/2005 | Selzer et al. | 600/450 |
| 2004/0260180 A1 * | 12/2004 | Kanai et al. | 600/449 |
| 2007/0032726 A1 | 2/2007 | Osaka et al. | |
| 2007/0055149 A1 * | 3/2007 | Suzuki et al. | 600/437 |
| 2007/0213614 A1 | 9/2007 | Suzuki et al. | |
| 2008/0021318 A1 | 1/2008 | Kato et al. | |
| 2009/0227867 A1 | 9/2009 | Suzuki et al. | |

FOREIGN PATENT DOCUMENTS

| | | |
|---|---|---|
| EP | 1 889 571 A1 | 2/2008 |
| JP | 10-005226 | 1/1998 |
| JP | 2000-229078 | 8/2000 |
| JP | 2004-159672 | 6/2004 |
| JP | 2005-118152 | 5/2005 |

(Continued)

OTHER PUBLICATIONS

International Search Report for corresponding International Application No. PCT/JP2008/002044 mailed Aug. 26, 2008.

*Primary Examiner* — James Kish
(74) *Attorney, Agent, or Firm* — Renner, Otto, Boisselle & Sklar LLP

(57) ABSTRACT

An ultrasonic diagnostic apparatus includes: a transmitting section for driving a probe to send out ultrasonic waves toward a subject one after another; a receiving section for getting an echo, produced as a result of reflection of each ultrasonic wave from the subject, received by the probe, thereby generating a received signal; a tissue tracking section for generating position tracking waveforms, each representing the positional displacement of an associated one of measuring points on the subject, based on the received signals; a boundary detecting section for determining the boundary location of the subject's tissue; a tracking waveform choosing section for choosing at least two position tracking waveforms, including the one associated with the boundary, from the position tracking waveforms by reference to at least one of the waveforms associated with the measuring points, the location of the boundary, and the amplitudes of the received signals; and a tissue attribute value calculating section for calculating a tissue attribute value of the subject using the position tracking waveforms chosen.

17 Claims, 7 Drawing Sheets

FOREIGN PATENT DOCUMENTS

| | | |
|---|---|---|
| JP | 2007-020724 | 2/2007 |
| WO | 2004/103185 A1 | 12/2004 |
| WO | 2006/011504 A1 | 2/2006 |
| WO | 2006/025364 A1 | 3/2006 |
| WO | 2006/129545 A1 | 12/2006 |
| WO | 2007/069650 A1 | 6/2007 |

* cited by examiner

ULTRASONOGRAPH THAT CHOOSES TRACKING WAVEFORMS FOR ATTRIBUTE VALUE CALCULATIONS

TECHNICAL FIELD

The present invention relates to an ultrasonic diagnostic apparatus for calculating some attribute value of a subject's tissue such as strain, elasticity and viscosity using ultrasonic waves.

BACKGROUND ART

An ultrasonic diagnostic apparatus is used to make a non-invasive checkup on a subject by irradiating him or her with an ultrasonic wave and analyzing the information contained in the echo signal, which is obtained as an ultrasonic echo from the subject. For example, a conventional ultrasonic diagnostic apparatus that has been used extensively converts the intensity of the echo signal into its associated pixel luminance, thereby presenting the subject's internal structure as a tomographic image. In this manner, the internal structure of the subject can be known.

Meanwhile, some people are attempting recently to track the motion of a subject's tissue more precisely and evaluate the strain and the elasticity, viscosity or any other physical (attribute) property of the tissue mainly by analyzing the phase of the echo signal.

Patent Document No. 1 discloses a method for tracking a subject's tissue highly precisely by sending out ultrasonic waves toward the same site of the subject a number of times at regular intervals to obtain multiple echo signals, calculating the instantaneous displacement of a local region of the subject based on a phase difference between the echo signals, and then adding the displacements together. Hereinafter, the subject tissue tracking method disclosed in Patent Document No. 1 will be described with reference to FIG. 5.

Suppose ultrasonic pulses are sent out toward the same site of the subject at intervals $\Delta T$ and ultrasonic echoes received are converted into electrical signals to obtain received signals $y1(t), y2(t), \ldots$ and $yn(t)$, where $1, 2, \ldots$ and $n$ indicates the order of transmission and reception that have been repeatedly performed at the intervals $\Delta T$ and $t$ indicates the time of reception with respect to the time of transmission which is represented by zero. In this case, the distance x from the source of reflection in the subject to the probe (which will be simply referred to herein as a "distance") and the time t of reception of the received signal with respect to the time of transmission satisfy the following Equation (1):

$$t=2x/C \quad (1)$$

where C represents the acoustic velocity of the medium.

The received signals $y1(t), y2(t), \ldots$ and $yn(t)$, which are functions of time, can be converted into $y1(x), y2(x), \ldots$ and $yn(x)$, which are functions of distance, by Equation (1). That is to say, the echo signal that has been reflected from the source of reflection, which is located at the distance x from the probe, is received in the amount of time t that is represented by Equation (1). Suppose there is a measuring point at a distance X and the measuring point has moved $\Delta X$ parallel to the traveling direction of the ultrasonic wave during the interval $\Delta T$. To calculate the magnitude of displacement $\Delta X$ of this measuring point during the interval $\Delta T$, according to Patent Document No. 1, an quadrature detection is carried out on $y1(x)$ and $y2(x)$ using a reference signal with a frequency f as shown in FIG. 6, thereby obtaining complex received signals $I1(x), Q1(x), I2(x)$ and $Q2(x)$. And correlation calculation and arctangent calculation are performed on those complex received signals, thereby calculating the phase difference $\Delta\theta$ between $y1(X)$ and $y2(X)$ at the distance X. And the displacement $\Delta X$ is calculated by the following Equation (2):

$$\Delta X=-C \cdot \Delta\theta/4\pi f \quad (2)$$

And by adding the displacement $\Delta X$ that has been calculated by Equation (2) to the original measuring point X, the position X' of the measuring point in $\Delta T$ is obtained by the following Equation (3):

$$X'=X+\Delta X \quad (3)$$

By repeatedly making this calculation, the measuring point on the subject can be tracked. As shown in FIG. 5, supposing the signal received next to $y2(X)$ is $y3(X)$, by substituting the phase difference $\Delta\theta'$ between $y2(X')$ and $y3(X')$ into Equation (2) and by substituting the displacement $\Delta X'$ obtained into Equation (3), the position X" of the measuring point in $2\Delta T$ can be obtained.

Patent Document No. 2 further develops the method of Patent Document No. 1 into a method of calculating the elasticity of a subject's tissue (e.g., an arterial wall, in particular). According to this method, first, an ultrasonic wave is transmitted from a probe 101 toward the vascular wall 302 of the subject 301 as shown in FIG. 7(a). And the echo signals, reflected from measuring points A and B that have been set on the same acoustic line on the vascular wall, are analyzed by the method of Patent Document No. 1, thereby tracking the motions of the measuring points A and B. FIG. 7(b) shows the tracking waveforms TA and TB of the measuring points A and B along with an electrocardiographic complex ECG. As shown in FIG. 7(b), the tracking waveforms TA and TB have the same periodicity as the electrocardiographic complex ECG, which indicates that the artery dilates and shrinks in sync with the cardiac cycle of the heart. More specifically, when the electrocardiographic complex ECG has outstanding peaks called "R waves", the heart starts to shrink, thus pouring blood flow into the artery and raising the blood pressure. As a result, the vascular wall is dilated rapidly. That is why soon after the R wave has appeared on the electrocardiographic complex ECG, the artery dilates rapidly and the tracking waveforms TA and TB rise steeply, too. After that, however, as the heart dilates slowly, the artery shrinks gently and the tracking waveforms TA and TB gradually fall to their original levels. The artery repeats such a motion cyclically.

The difference between the tracking waveforms TA and TB is represented as a waveform W showing a variation in thickness between the measuring points A and B. Supposing the maximum variation of the thickness change waveform W is $\Delta W$ and the reference thickness between the measuring points A and B during initialization (i.e., the end of the diastole) is Ws, the magnitude of maximum strain $\epsilon$ between the measuring points A and B is calculated by the following Equation (4):

$$\epsilon=\Delta W/Ws \quad (4)$$

As this strain is caused due to the difference between the blood pressures applied to the vascular wall, the elasticity E between the measuring points A and B is given by:

$$E=\Delta P/\epsilon=\Delta P \cdot Ws/\Delta W \quad (5)$$

where $\Delta P$ is the blood pressure difference at this time.

Therefore, by measuring the elasticity E for multiple spots on a tomographic image, an image representing the distribution of elasticities can be obtained. If an atheroma 303 has been created in the vascular wall as shown in FIG. 7(a), the atheroma 303 and its surrounding vascular wall tissue have different elasticities. That is why if an image representing the distribution of elasticities is obtained, important information can be obtained in inspecting the attribute of the atheroma (e.g., how easily the atheroma may rupture, among other things).

FIG. 8 schematically illustrates exemplary results of calculations that have been made to evaluate the elasticity of a vascular wall by the method disclosed in Patent Document No. 2. On the monitor (i.e., on the paper on which FIG. 8 is drawn), displayed is the vascular wall's monochrome tomographic image 200. A region of interest ROI has been set on the vascular wall portion and a two-dimensional elasticity image 201 representing the distribution of elasticities in a part of the region of interest ROI corresponding to the vascular wall is superimposed in colors on the tomographic image 200. The monochrome tomographic image 200 is displayed at monochromatic gray scales corresponding to the reflection intensities along with a scale 202 indicating the reflection intensities. On the other hand, the elasticity image 201 is displayed in color tones corresponding to the elasticity values along with a scale 203 indicating the elasticity values. Also displayed under the monochrome tomographic image 200 is a biomedical signal waveform 204 such as an electrocardiogram.

However, not all of these tissue attribute values thus obtained are reliable ones but some of them are quite unreliable or inaccurate. Such values would have been obtained probably because the same tissue could not be tracked accurately or its attribute could not be evaluated accurately due to the occurrence of some noise during the measurement, the shift of the measuring point away from the acoustic line, the influence of speckle, and the ringing echo from an intense reflection source.

For example, an atheroma is included within the region of interest ROI shown in FIG. 8. It is known that an atheroma has a hard skin and a soft content. However, the two-dimensional elasticity image 201 shown in FIG. 8 indicates that there is an abnormally soft portion such as liquid and an extraordinarily hard portion that hardly deforms. And those portions indicate clearly wrong results of measurement.

To cope with such problems, Patent Document No. 3 discloses an ultrasonic diagnostic apparatus including display value evaluating means for evaluating the display value of a strain elasticity image generated based on various kinds of data that have been generated while the strain elasticity image (corresponding to the tissue attribute value) is produced. According to Patent Document No. 3, based on the results of evaluation obtained by the display value evaluating means, image information that has been graded with the strain elasticity value is displayed in an area with display value, while either the same piece of image information or a strain elasticity value is displayed in an area with no display value. According to this method, elasticity images with low degrees of reliability can be eliminated and only elasticity images with high degrees of reliability can be displayed.

On the other hand, according to Patent Document No. 4, the magnitude of shrinkage or expansion of the object of measurement between two normal end points is calculated based on the ordinary velocity (or displacement) between those two normal end points, thereby obtaining elasticity (corresponding to a tissue attribute value). That is to say, data with low reliability or low accuracy are eliminated right after the displacement has occurred and the tissue attribute value is calculated based on only displacement data with high reliability. According to this method, in regions from which such data with low reliability have been eliminated, the vertical resolution certainly decreases but accurate tissue attribute value can be obtained eventually.

Patent Document No. 1: Japanese Patent Application Laid-Open Publication No. 10-5226
Patent Document No. 2: Japanese Patent Application Laid-Open Publication No. 2000-229078
Patent Document No. 3: Japanese Patent Application Laid-Open Publication No. 2005-118152
Patent Document No. 4: Japanese Patent Application Laid-Open Publication No. 2004-159672

DISCLOSURE OF INVENTION

Problems to be Solved by the Invention

According to the method disclosed in Patent Document No. 2, however, the image representing the distribution of tissue attribute values obtained has missing parts here and there, and the sum of the amounts of data with high reliability could be the smaller depending on the situation. FIG. 9 schematically illustrates an exemplary result of measurement that was carried out on a vascular wall by the method disclosed in Patent Document No. 3. As shown in FIG. 9, among a number of unit areas that form the two-dimensional distribution image, approximately a half of them turned out to be unreliable ones, thus making this image very difficult to look at.

On the other hand, according to the method disclosed in Patent Document No. 4, the number of missing parts can be certainly reduced but still there are some missing parts albeit locally. FIG. 10 schematically illustrates an exemplary result of measurement that was carried out on a vascular wall by the method disclosed in Patent Document No. 4. As shown in FIG. 10, the acoustic line around the center and the rightmost acoustic line have less than one measuring point with high reliability, and therefore, display no tissue attribute values because the tissue attribute values cannot be defined in such a situation. It can also be seen that in either the upper half or the lower half of the vascular wall, no tissue attribute values can be defined, either, and some acoustic lines have missing parts, too.

It is therefore an object of the present invention to provide an ultrasonic diagnostic apparatus that can obtain the tissue attribute values of a subject more accurately.

Means for Solving the Problems

An ultrasonic diagnostic apparatus according to the present invention includes: a transmitting section for driving a probe so that the probe sends out ultrasonic waves toward a subject one after another; a receiving section for getting an echo, which has been produced as a result of reflection of each said ultrasonic wave from the subject, received by the probe, thereby generating a received signal; a tissue tracking section for generating position tracking waveforms, each of which represents the positional displacement of an associated one of measuring points that have been set on the subject, based on the received signals; a boundary detecting section for determining the boundary location of the subject's tissue; a tracking waveform choosing section for choosing at least two position tracking waveforms, including the one associated with the boundary, from the multiple position tracking waveforms by reference to at least one of the position tracking waveforms associated with the multiple measuring points, the location of the boundary, and the amplitudes of the received signals; and a tissue attribute value calculating section for calculating a tissue attribute value of the subject using the position tracking waveforms that have been chosen.

In one preferred embodiment, the tracking waveform choosing section excludes a position tracking waveform with noise, a position tracking waveform representing a different displacement direction from the others, or a position tracking waveform with a different fundamental shape from the others.

In this particular preferred embodiment, the tracking waveform choosing section determines the position tracking waveform to exclude by pattern matching, correlation coefficients, difference calculation or fast Fourier transform.

In another preferred embodiment, if position tracking waveforms associated with two or more adjacent measuring points are substantially identical with each other, then the tracking waveform choosing section chooses only one of those substantially identical waveforms.

In a specific preferred embodiment, the tracking waveform choosing section chooses a position tracking waveform that is associated with a measuring point that has produced a received signal with the greatest amplitude.

In still another preferred embodiment, the tracking waveform choosing section excludes position tracking waveforms that do not satisfy a constraint imposed by the shape of the subject's tissue.

In this particular preferred embodiment, the tissue has the shape of a cylinder, the measuring points are set in the radial direction of the cylinder, and the tracking waveform choosing section excludes any position tracking waveform if the amplitudes of all the other position tracking waveforms associated with multiple measuring points, but that position tracking waveform, decrease from an inner point of the cylinder toward an outer point thereof.

In yet another preferred embodiment, the tracking waveform choosing section excludes position tracking waveforms that do not satisfy a constraint imposed by a function of the subject's tissue.

In a specific preferred embodiment, the tissue is a vascular wall, the measuring points are set in the axial direction of the vascular wall, and the tracking waveform choosing section excludes any position tracking waveform if all the other position tracking waveforms associated with the multiple measuring points, but that position tracking waveform, represent timings of shrinkage and dilation that are delayed sequentially from some central point toward a peripheral point.

In another preferred embodiment, the tissue is the heart, the measuring points are set in the thickness direction of its cardiac muscle, and the tracking waveform choosing section excludes any position tracking waveform if all the other position tracking waveforms associated with the multiple measuring points, but that position tracking waveform, represent either timings of shrinkage that are delayed sequentially from some inner point on the cardiac muscle toward an outer point on the muscle or timings of dilation that are delayed sequentially from some outer point on the cardiac muscle toward an inner point on the muscle.

In yet another preferred embodiment, the subject has been deformed under external force and the tracking waveform choosing section excludes position tracking waveforms that do not satisfy a constraint imposed by the point, direction, or method of applying the force.

In this particular preferred embodiment, the external force is applied by pressing the probe down toward the subject, and the tracking waveform choosing section excludes position tracking waveforms, of which the amplitudes do not increase as the point of measurement is set at a greater distance from the probe.

In yet another preferred embodiment, the ultrasonic diagnostic apparatus further includes a user interface that allows the user to specify the boundary location, and the boundary detecting section determines the location that has been specified by the user to be the boundary.

In yet another preferred embodiment, the boundary detecting section is connected to an external modality and gets boundary information from the modality.

In yet another preferred embodiment, the tracking waveform choosing section chooses a position tracking waveform that is associated with a measuring point on the tissue with respect to the boundary detected by the boundary detecting section.

In yet another preferred embodiment, the ultrasonic diagnostic apparatus further includes a display section to display the tissue attribute values.

In a specific preferred embodiment, the display section displays the tissue attribute values as a two-dimensional distribution image.

In this particular preferred embodiment, the display section displays a histogram of the tissue attribute values.

Effects of the Invention

As described above, the ultrasonic diagnostic apparatus of the present invention chooses at least two position tracking waveforms, including the one associated with the boundary, from multiple position tracking waveforms by reference to at least one of the position tracking waveforms associated with the multiple measuring points, the location of the boundary, and the amplitudes of the received signals, and calculates the tissue attribute value using the position tracking waveform chosen. As a result, the measurement data can be selected more accurately and more appropriately than in the prior art, and accurate tissue attribute with no improper data can be obtained. On top of that, as the tissue attribute value is calculated using the position tracking waveform that is associated with the boundary, the tissue attribute value is never calculated over two different tissues. That is to say, an accurate tissue attribute value can be obtained for each tissue. Furthermore, the tissue attribute values can be obtained accurately over the entire region of interest without producing any missing parts either dispersively or just locally.

Figure 1:
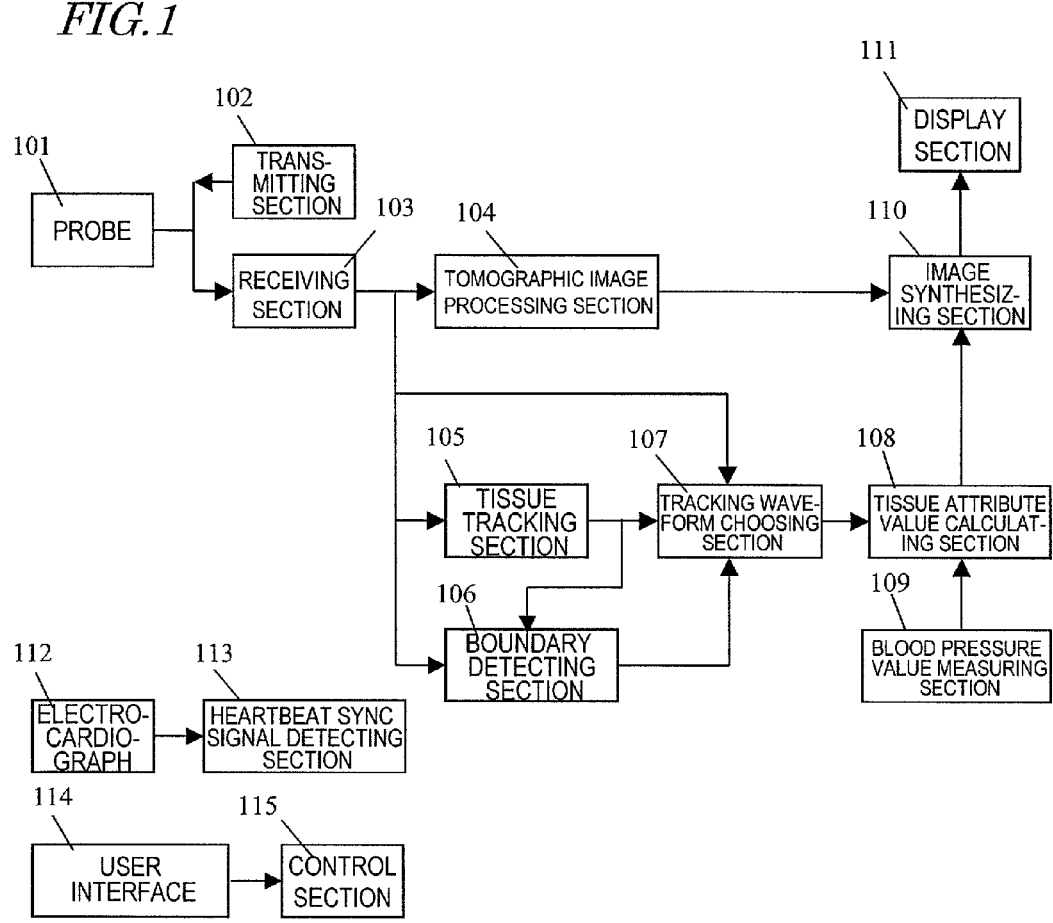
FIG. 1 is a block diagram illustrating an ultrasonic diagnostic apparatus as a preferred embodiment of the present invention.
Figure 2:
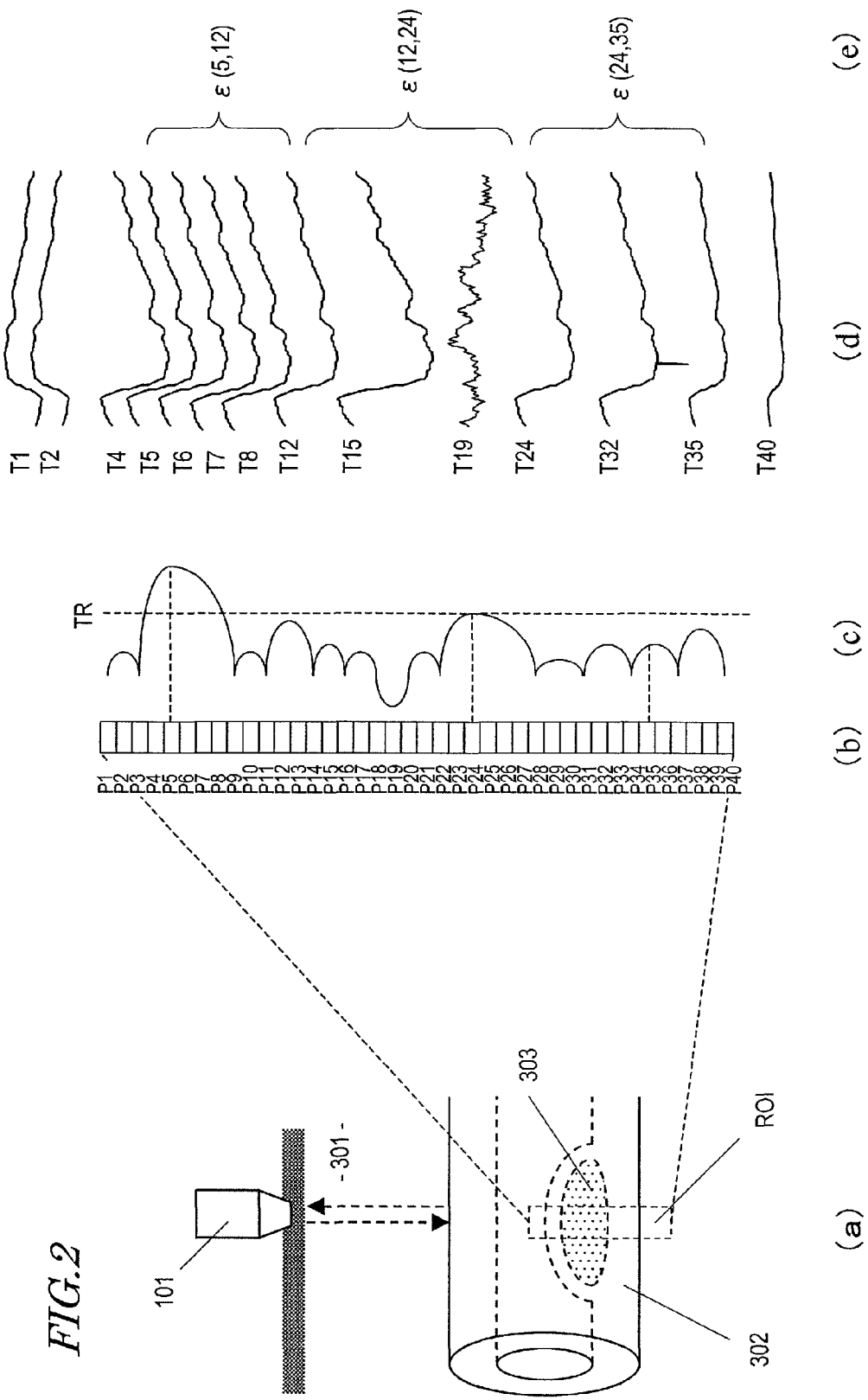

Portions (a) through (e) of FIG. 2 illustrate how the ultrasonic diagnostic apparatus shown in FIG. 1 operates.

Figure 3:
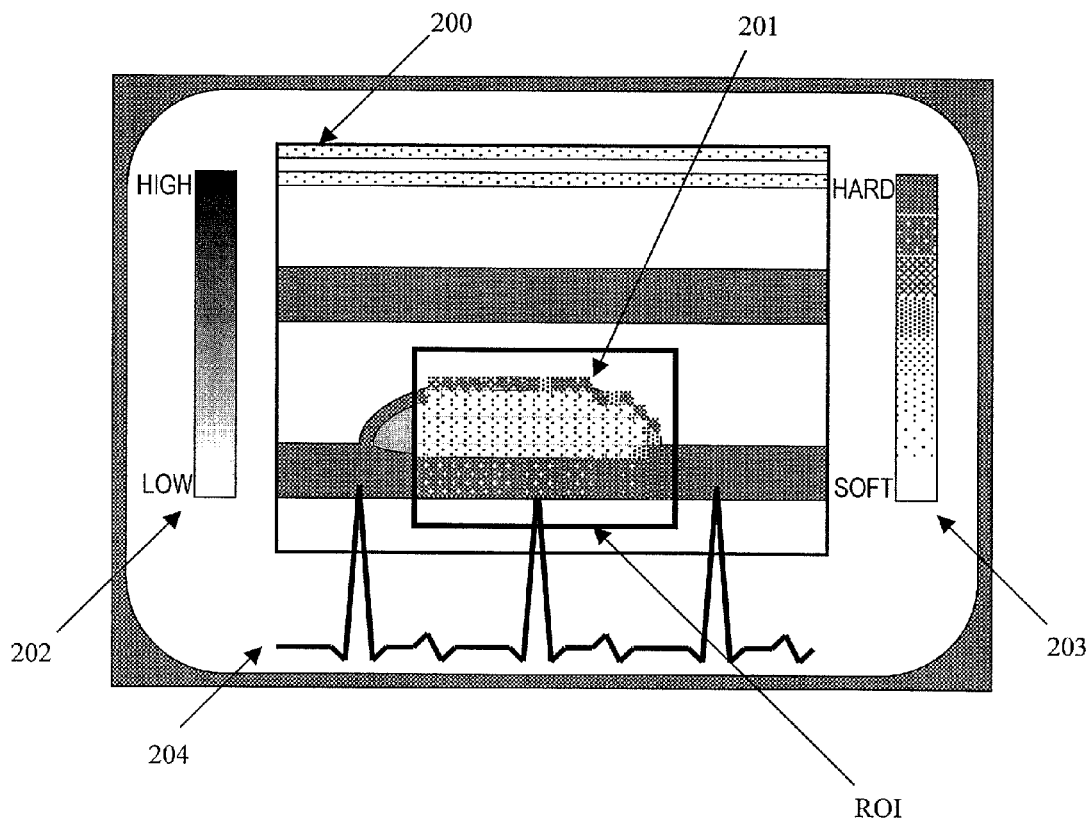

FIG. 3 schematically illustrates exemplary results of measurements that were obtained by the ultrasonic diagnostic apparatus shown in FIG. 1.

Figure 4:
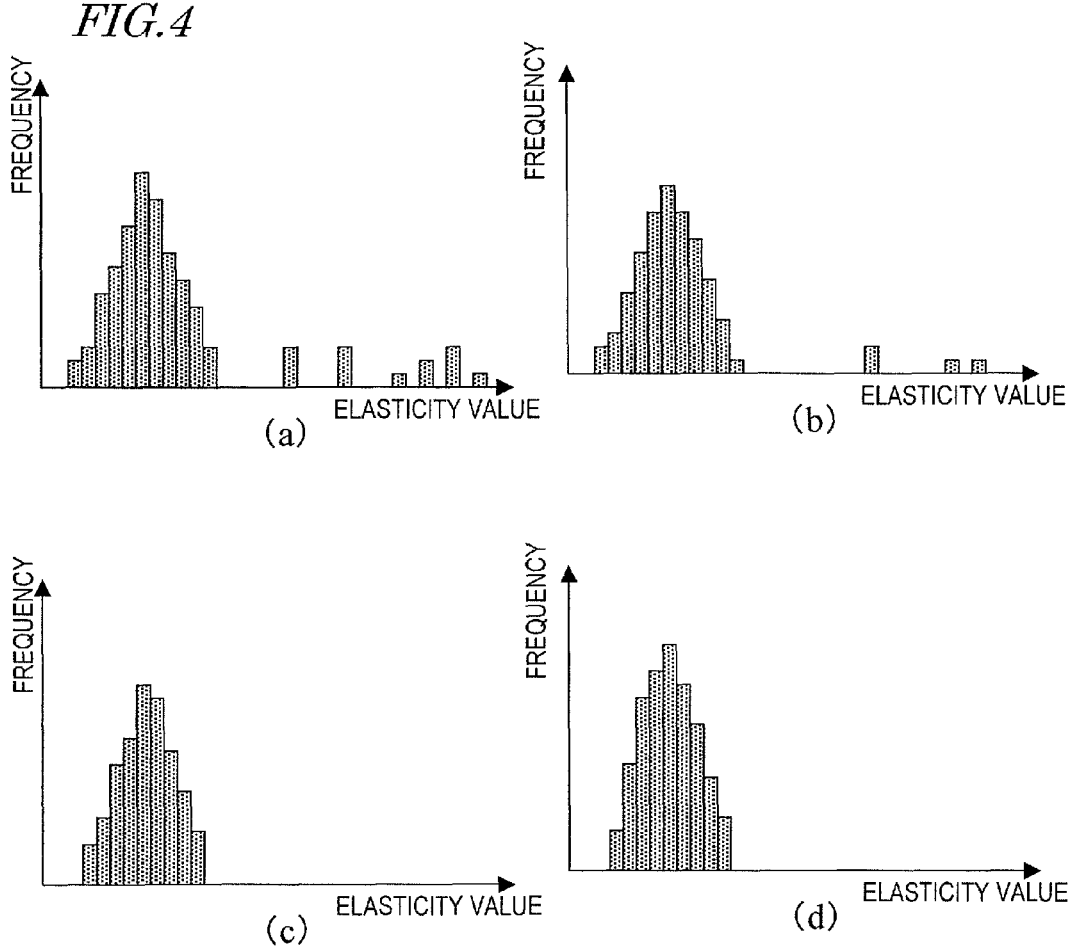

FIGS. 4(a) through 4(c) are histograms representing the elasticity values that were obtained by a conventional ultrasonic diagnostic apparatus and FIG. 4(d) is a histogram representing the elasticity values obtained by the ultrasonic diagnostic apparatus shown in FIG. 1.

Figure 5:
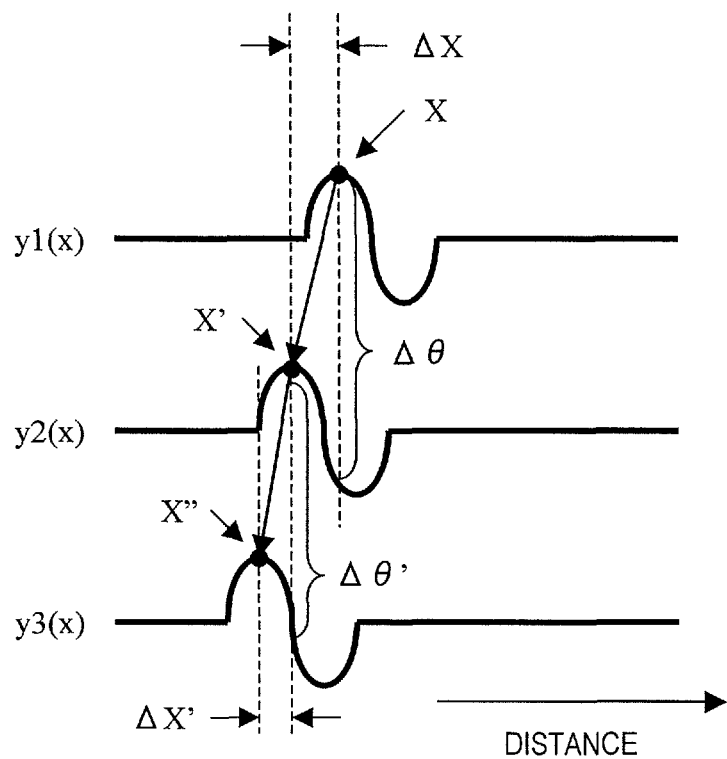

FIG. 5 illustrates how to track a position.

Figure 6:
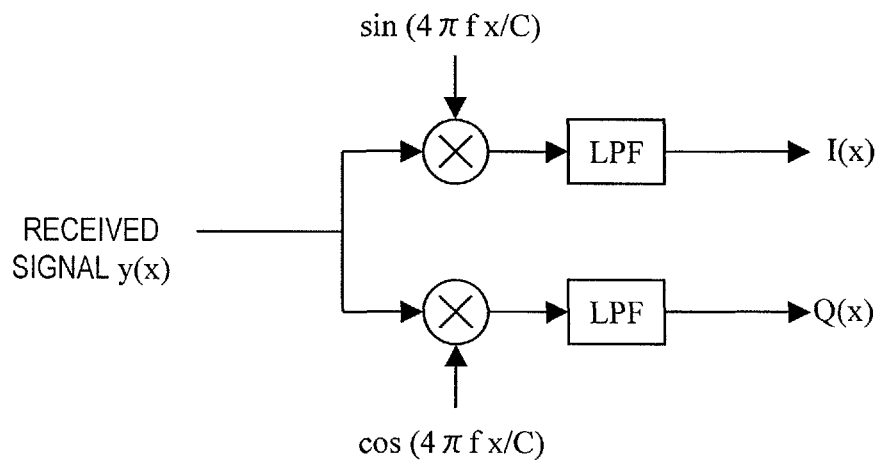

FIG. 6 illustrates an example of an quadrature detector.

Figure 7:
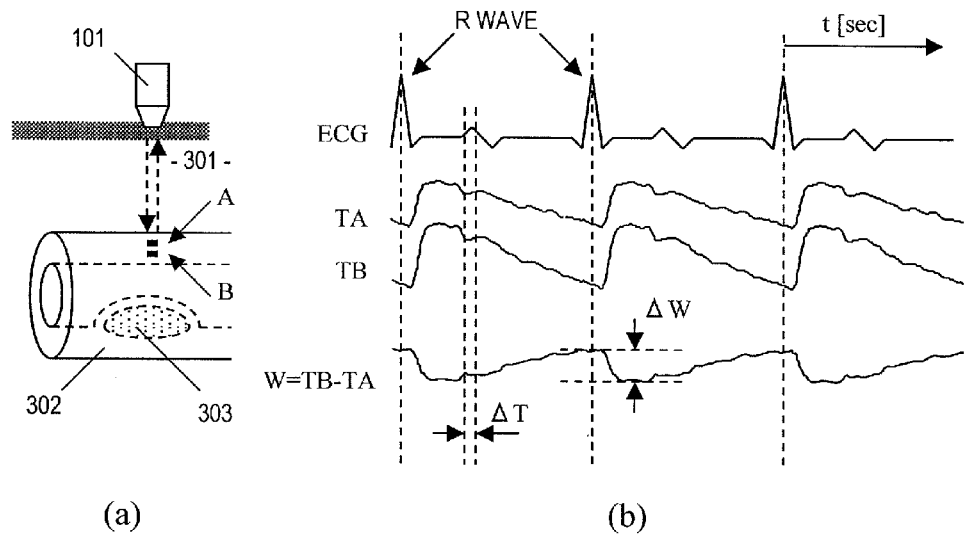

FIGS. 7(a) and 7(b) illustrate a conventional method for measuring the tissue attribute value of a vascular wall using ultrasonic waves.

Figure 8:
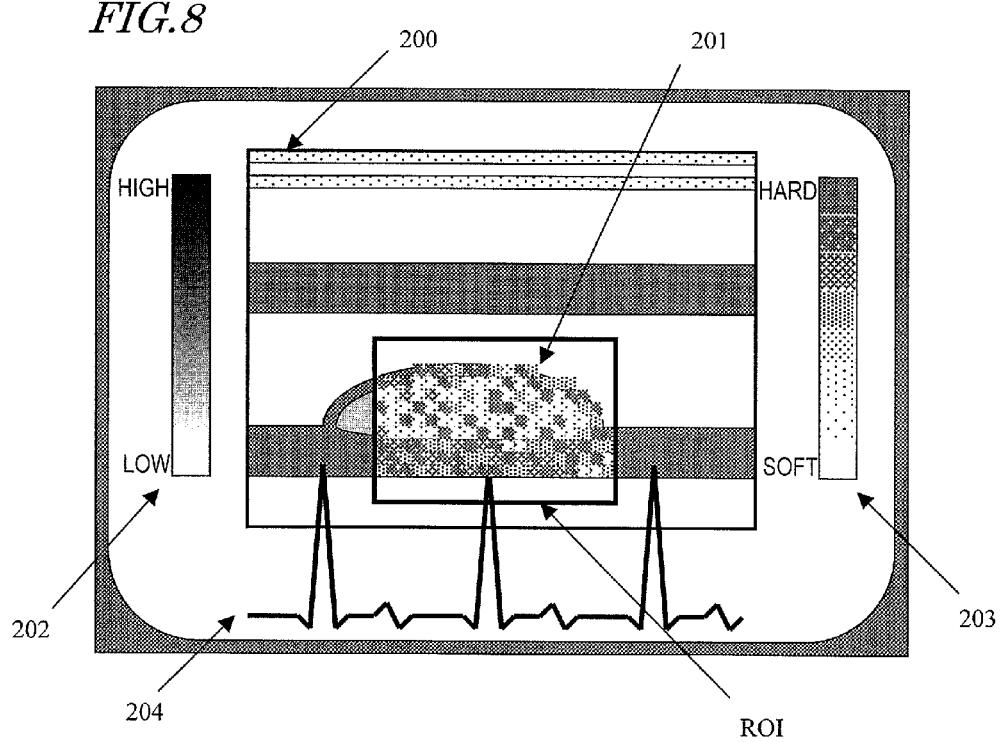

FIG. 8 illustrates exemplary results of measurement obtained by a conventional ultrasonic diagnostic apparatus.

Figure 9:
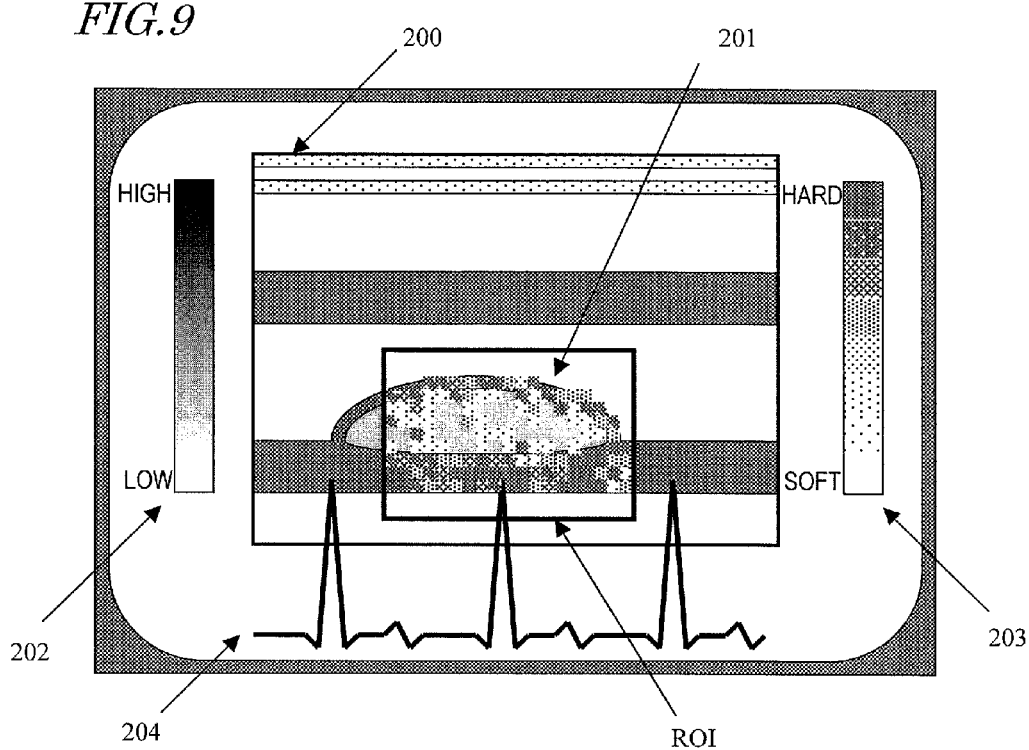

FIG. 9 illustrates exemplary results of measurement obtained by a conventional ultrasonic diagnostic apparatus.

Figure 10:
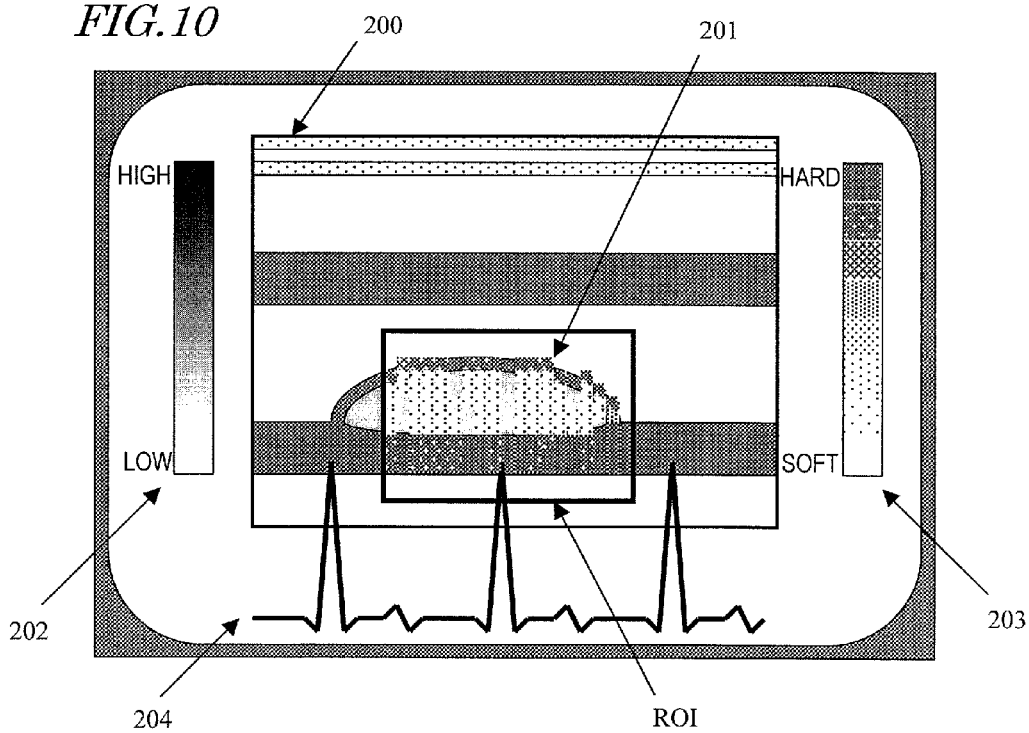

FIG. 10 illustrates exemplary results of measurement obtained by a conventional ultrasonic diagnostic apparatus.

DESCRIPTION OF REFERENCE NUMERALS 101 probe
102 transmitting section
103 receiving section
104 tomographic image processing section
105 tissue tracking section
106 boundary detecting section
107 tracking waveform choosing section
108 tissue attribute value calculating section
109 blood pressure value measuring section
110 image synthesizing section
111 display section
112 electrocardiograph
113 heartbeat sync signal detecting section
114 user interface
115 control section

BEST MODE FOR CARRYING OUT THE INVENTION

Hereinafter, preferred embodiments of an ultrasonic diagnostic apparatus according to the present invention will be described with reference to the accompanying drawings.

FIG. 1 is a block diagram illustrating an ultrasonic diagnostic apparatus according to the present invention. As shown in FIG. 1, the ultrasonic diagnostic apparatus includes a transmitting section 102, a receiving section 103, a tomographic image processing section 104, a tissue tracking section 105, a boundary detecting section 106, a tracking waveform choosing section 107, a tissue attribute value calculating section 108, an image synthesizing section 110, a display section 111 and a heartbeat sync signal detecting section 113. The apparatus further includes a control section 115 for controlling all of these components and a user interface 114 such as a keyboard, a track ball, a switch, a button, a key or a lever with which the user can enter his or her command or preferred settings. A probe 101 for transmitting and receiving an ultrasonic wave is connected to the ultrasonic diagnostic apparatus. An electrocardiograph 112 is preferably connected to the heartbeat sync signal detecting section 113.

In accordance with the instruction given by the control section 115, the transmitting section 102 generates a high-voltage electrical signal to transmit one after another that drives the probe 101 at a specified timing. The probe 101 gets the electrical signal to transmit that has been generated by the transmitting section 102 converted by its internal piezoelectric transducer into an ultrasonic wave and sends out the ultrasonic wave toward a subject, and also detects an ultrasonic echo that has been reflected by an internal organ of the subject and converts the echo into an electrical signal. A number of piezoelectric transducers are usually arranged in the probe 101. By changing the piezoelectric transducers to use, the timing to apply a voltage to the piezoelectric transducers, or the voltages themselves, the probe 101 controls the position and direction of radiation of the ultrasonic waves to transmit and receive.

The receiving section 103 amplifies the signal that has been received by the probe 101, delays appropriately the signals supplied from the respective piezoelectric transducers, and adds those received signals together. In this manner, the receiving section 103 detects only an ultrasonic wave that has been reflected from a predetermined point or only an ultrasonic wave that has come from a predetermined direction.

Although not shown, the tomographic image processing section 104 includes various types of filters, detectors, logarithmic amplifiers, scanning converters and other signal/image processors, and analyzes mainly the amplitude of the received signal, thereby presenting a tomographic image of the subject.

The tissue tracking section 105 may include an ASIC, an FPGA, a DSP, a CPU or a memory and tracks the positional displacement of each of multiple measuring points that have been set on the subject parallel to the ultrasonic wave transmitting and receiving direction, which is the acoustic line direction of the ultrasonic wave, by the position tracking method of Patent Document No. 1, for example, thereby generating position tracking waveforms.

The boundary detecting section 106 locates the tissue's boundary based on either the received signal supplied from the receiving section 103 or the position tracking waveform of the subject's tissue that has been tracked by the tissue tracking section 105. When the received signal is used, the boundary detecting section 106 may determine a measuring point, at which the amplitude of the received signal is equal to or greater than a predetermined value, to be the boundary. This is because impedance changes at the tissue's boundary and the reflectance of an ultrasonic wave from the boundary is usually higher than anywhere else.

Optionally, the location of the boundary may also be determined by a point that has been specified by the user. Specifically, the user may specify some point on the tomographic image being displayed on the display section 111 using the user interface 114. In response, the boundary detecting section 106 finds a measuring point on the tomographic image that corresponds to the specified point, thereby determining the location of the boundary. Alternatively, the boundary detecting section 106 may be connected to an external modality such as a CT scanner or an MRI scanner and may determine the location of the boundary of the subject based on the image information that has been received from the modality.

The tracking waveform choosing section 107 chooses at least two position tracking waveforms, including the one associated with the boundary, from the multiple position tracking waveforms by reference to at least one of the amplitude of the received signal supplied from the receiving section 103, the position tracking waveforms generated by the tissue tracking section 105 for the respective measuring points, and the location of the boundary that has been determined by the boundary detecting section 106.

The tissue attribute value calculating section 108 receives the subject's blood pressure value form the blood pressure value measuring section 109, which may be provided as an external member. In this case, the blood pressure value measuring section 109 may be an independent blood pressure manometer, or may be built in the ultrasonic diagnostic apparatus, or may be controlled by the ultrasonic diagnostic apparatus. Optionally, the user may enter the subject's blood pressure value into the tissue attribute value calculating section 108 using the user interface 114.

The tissue attribute value calculating section 108 calculates a value representing a tissue attribute based on the position tracking waveforms that have been chosen by the tracking waveform choosing section 107. In this case, the "value representing the tissue attribute" may be either the strain represented by Equation (3) or the elasticity calculated by Equation (4) based on the blood pressure value measured by the blood pressure value measuring section 109 and the strain. The tissue attribute value calculating section 108 may output those tissue attribute values as a set of numerical values to the display section 111. Alternatively, those values may also be output as a two-dimensional distribution image, representing the distribution of those tissue attribute values, or a graph such as a histogram representing the tissue attributes.

The image synthesizing section 110 synthesizes together at least the tomographic image and the numerical values, two-dimensional distribution image, or histogram that has been supplied as representing tissue attribute values from the tissue attribute value calculating section 108. And the display section 111 displays the synthetic image thus produced. The display section 111 is typically a monitor such as a CRT or an LCD. However, the display section 111 may also be a printing device such as a printer as long as the tomographic image and the numerical values or distribution image representing the tissue attributes can be displayed on it so as to be easily viewable to the human eye.

The heartbeat sync signal detecting section 113 detects a signal, which rises and falls synchronously with the heartbeat. The heartbeat sync signal may be an R wave trigger pulse detected by the electrocardiograph 112 or may have been obtained by analyzing either the tissue tracking waveform obtained by the tissue tracking section 105 or the tomographic image obtained by the tomographic image processing section 104. Or any other heartbeat sync signal may also be used. The heartbeat sync signal that has been obtained by the heartbeat sync signal detecting section 113 is output to the tissue tracking section 105 and used as a measuring point initializing signal. The heartbeat sync signal is also output to the tissue attribute value calculating section 108, the boundary detecting section 106 and the tracking waveform choosing section 107 and used as a timing signal to calculate the tissue attribute values or the location of the boundary.

Hereinafter, it will be described in detail with reference to FIG. 2 how the ultrasonic diagnostic apparatus with such a configuration operates (and exactly how the boundary detecting section 106, the tracking waveform choosing section 107, and the tissue attribute value calculating section 108, which are the principal sections of the present invention, operate, among other things). In the example to be described below, the vascular wall is supposed to be included in the subject. However, the ultrasonic diagnostic apparatus of the present invention is not always applied to the vascular wall. Also, in the example to be described below, the tissue attribute values are supposed to be strain and elasticity values but could also be viscosity as well.

As shown in portion (a) of FIG. 2, the ultrasonic wave that has been sent out from the probe 101 is reflected from the vascular wall 302 and then returns to the probe 101 again. A region of interest (ROI) has been defined in advance on a portion of the vascular wall 302 as a region where the tissue attribute values need to be calculated. As shown in portion (b) of FIG. 2, multiple (e.g., 40 in portion (b) of FIG. 2) measuring points Pn have been set in the depth direction within the region of interest ROI. Portion (c) of FIG. 2 shows the distribution of intensities of the received signal in the depth direction within the region of interest. Portion (d) of FIG. 2 shows the position tracking waveforms Tn associated with the respective measuring points Pn. And portion (e) of FIG. 2 shows the tissue attribute values (e.g., strain values) $\epsilon(n, m)$ obtained by processing the position tracking waveforms. It should be noted that $\epsilon(n, m)$ represents the magnitude of strain between the measuring points n and m. Portion (b) of FIG. 2 shows only the measuring points that have been set on a single acoustic line. Actually, however, the ultrasonic diagnostic apparatus of the present invention transmits and eventually scans multiple ultrasonic waves, thereby calculating the tissue attribute values of the subject two-dimensionally.

The boundary detecting section 106 may locate the boundary of the vascular wall, which is an exemplary subject's tissue, by the amplitude of the received signal as shown in portion (c) of FIG. 2, for example. More specifically, by paying attention to the fact that the reflectance of an ultrasonic wave from the boundary is higher than anywhere else and the received signal comes to have an increased amplitude, the boundary detecting section 106 may determine the threshold value TR in advance and determine a measuring point, at which the amplitude of the received signal exceeds the threshold value TR, to be the boundary. In this manner, the boundary between the blood flow and the intima may be determined to be the measuring point P5 and the boundary between the media and the adventitia may be determined to be the measuring point P24.

The threshold value does not have to be a constant value but may also vary through the given measuring period. Also, the boundary does not always have to be located by determining whether the amplitude of the received signal exceeds the threshold value or not but may also be determined by finding where the waveform changes among multiple position tracking waveforms associated with multiple measuring points. This is because if the tissues are different, the measuring point should be displaced differently.

According to the method that involves the threshold value processing just described, the boundary between the blood flow and the intima and the boundary between the media and the adventitia can be determined as shown in portions (a) and (c) of FIG. 2 but the boundary between the adventitia and a peripheral tissue cannot be determined. This is because the boundary between the adventitia and the peripheral tissue is essentially indefinite and will reflect the ultrasonic wave too little to have measuring points where the threshold value is exceeded. In that case, the boundary may be set by the user with the user interface 114. Alternatively, image information may be received from another modality such as a CT scanner or an MRI scanner and the boundary may be determined based on that image information. In this example, the measuring point P35 is supposed to be specified as the boundary between the adventitia and the periphery tissue by the user.

The tracking waveform choosing section 107 chooses position tracking waveforms associated with measuring points that are used by the tissue attribute value calculating section 108 to calculate the tissue attribute values. If the subject is deformed periodically, it is preferred that respective parts of the position tracking waveforms associated with the measuring points be obtained for one period and used for the selection processing to be described later. If the tissue attribute value is either strain or elasticity, that one period of each position tracking waveform extracted preferably includes its maximum and minimum values. And if the subject includes the vascular wall, then that one period preferably includes S- and P-wave periods of the subject's pulse wave.

The tissue tracking section 105 can track the motion of the subject's tissue rather accurately. But due to the influence of noise, for example, the position tracking waveform could be inaccurate or the tissue attribute value could be calculated improperly due to the received echo signal or the property of the object.

For example, the position tracking waveform T32 associated with the measuring point P32 has a spike noise as shown in portion (d) of FIG. 2. And the tissue attribute value to be calculated based on such a waveform should be inaccurate. That is why the position tracking waveform T32 is excluded as an inappropriate one.

Also, the position tracking waveforms T1 and T2 associated with the measuring points P1 and P2 are displaced in the opposite direction to the other position tracking waveforms T4 through T40 associated with the measuring points P4 through P40. This is because the waveforms T1 and T2 are obtained by tracking multiple echoes from the vascular near wall, which moves in the opposite direction to the vascular far wall. Anyway, the tissue attribute values to be calculated based on such position tracking waveforms T1 and T2 should be inaccurate. That is why the position tracking waveforms T1 and T2 are excluded as inappropriate ones.

Furthermore, the position tracking waveform T19 associated with the measuring point P19 has a different fundamental shape from the other waveforms. This is probably because the received signal has too small amplitude at the measuring point P19 to obtain sufficient information or to track the tissue well or even because the noise may have been tracked by mistake as shown in portion (c) of FIG. 2. And the tissue attribute value to be calculated based on the position tracking waveform T19 should also be inaccurate. That is why the position tracking waveform T19 is also excluded as an inappropriate one.

The position tracking waveform with noise, the position tracking waveform that is displaced in a different direction from the others, and the position tracking waveform that has a different fundamental shape from the others can be detected by calculating the difference between the waveforms by pattern matching, correlation coefficients, or difference calculation, for example. Optionally, the processing may also be carried out in a frequency range by fast Fourier transform (FFT).

Furthermore, as shown in portion (d) of FIG. 2, the position tracking waveforms T4 through T8 associated with the measuring points P4 through P8 have substantially the same shape and the same timing of displacement. This is because the received signals associated with these measuring points P4 through P8 are ringing echo signals obtained from the same source of reflection. If the tissue attribute value were obtained between these measuring points P4 through P8, then the strain would be zero, the elasticity would be infinite, and no tissue attribute value could be obtained properly. That is why if multiple identical position tracking waveforms were generated from an echo signal from a single source of reflection for multiple measuring points in this manner, only one of those position tracking waveforms should be chosen. For instance, if the position tracking waveforms T4 through T8 had been obtained as shown in portion (d) of FIG. 2, then the position tracking waveform T5 associated with the measuring point P5 at which the received signal has the greatest amplitude and the highest intensity may be adopted and the other position tracking waveforms T4 and T6 to T8 may be excluded. This is because the greater the amplitude of a received signal and the higher its intensity, the less easily the signal is susceptible to noise and the more accurately the measurement can be done.

Furthermore, position tracking waveforms that do not satisfy the constraint imposed by the shape of the subject's tissue may also be excluded. This is because if any position tracking waveform varied in a totally unexpected pattern considering the shape of the subject's tissue, then that position tracking waveform should not represent the displacement of the measuring point accurately. For example, the vascular wall has a cylindrical shape, and if any pressure (such as blood pressure) were internally applied to the vascular wall, then an external portion of the vascular wall would be strained less than an internal portion thereof (i.e., the external portion would be displaced less than the internal portion). Also, if the vascular wall were moving concentrically around its axis, then the position tracking waveform T15 associated with the measuring point P15 should have greater amplitude than the position tracking waveform T12 associated the inner measuring point P12 as shown in portion (d) of FIG. 2. That is why the position tracking waveform T15 should be excluded as an inappropriate one.

The tracking waveform choosing section 107 excludes those inappropriate position tracking waveforms and outputs only the remaining position tracking waveforms to the tissue attribute value calculating section 108 as the best position tracking waveforms to calculate the tissue attribute value accurately. In the example illustrated in portion (d) of FIG. 2, only the position tracking waveforms T5, T12 and T24 are chosen as the best position tracking waveforms and output to the tissue attribute value calculating section 108.

Furthermore, the tracking waveform choosing section 107 chooses a position tracking waveform associated with the boundary that has been detected by the boundary detecting section 106 and outputs it to the tissue attribute value calculating section 108. As a result, even if the vascular wall were too thin to choose the best measuring point, the tracking waveform associated with the boundary should never fail to be chosen and output to the tissue attribute value calculating section 108. That is why the tissue attribute value would never be calculated over two different tissues and an accurate tissue attribute value should be obtained within each tissue. If the boundary positions have been determined to be P5, P24 and P35 as already described with reference to portion (c) of FIG. 2, then the position tracking waveforms T5, T24 and T35 are chosen as the best position tracking waveforms and output to the tissue attribute value calculating section 108.

It should be noted that the measuring points P1 to P4, which are located inside of the measuring point P5 (or over the measuring point P5 in FIG. 2) that represents the intima-media boundary, are in the blood flow inside the blood vessel. On the other hand, the measuring points P36 to P40, which are located outside of the measuring point P35 (or under the measuring point P35 in FIG. 2) that represents the adventitia-peripheral tissue boundary, are in the extravascular tissue. There is no need to obtain the tissue attribute values at any of these points. As described above, by determining the location of the boundary, choosing only measuring points that are located in the desired tissue with respect to the boundary, and excluding the unnecessary measuring points that are located in the other region with respect to the boundary in this manner, the complexity of computations can be cut down.

The tissue attribute value calculating section 108 calculates the tissue attribute values based on only the position tracking waveforms provided by the tracking waveform choosing section 107. Specifically, as shown in portion (e) of FIG. 2, the tissue attribute value calculating section 108 calculates the strain $\epsilon$ (5, 12) between the measuring points P5 and P12 based on the position tracking waveforms T5 and T12, the strain $\epsilon$ (12, 24) between the measuring points P12 and P24 based on the position tracking waveforms T12 and T24, and the strain $\epsilon$ (24, 35) between the measuring points P24 and P35 based on the position tracking waveforms T24 and T35, respectively. In addition, the tissue attribute value calculating section 108 also calculates the elasticity based on the difference between the highest and lowest blood pressures provided by the blood pressure value measuring section 109.

A procedure like this is also carried out on the other acoustic lines, thereby obtaining the two-dimensional distribution of tissue attribute values. FIG. 3 schematically illustrates exemplary results of measurements that were obtained as described above from a blood vessel with an atheroma. Compared to FIG. 8 representing the results of measurements that were carried out in accordance with Patent Document No. 3, the vertical resolution is somewhat lower but the elasticity can be obtained more accurately. And compared to FIG. 9 representing the results of measurements that were carried out in accordance with Patent Document No. 4, the elasticity can be obtained accurately over the entire vascular wall without missing data anywhere.

FIGS. 4(a) through 4(d) are histograms representing the subject's elasticity values that were obtained by measurements. Specifically, FIG. 4(a) is a histogram representing the elasticities that were measured by the method disclosed in Patent Document No. 2. As shown in FIG. 4(a), unrealistic elasticities that are too high to be true were obtained anyway. The average, variance and other stats of elasticities calculated by that method should include such unrealistic high values, and therefore, cannot be called accurate ones. FIG. 4(b) is a histogram representing other elasticities that were measured by the method disclosed in Patent Document No. 3. It can be seen that some of those unrealistic elasticities have been certainly removed but that the distribution of low elasticities has shrunk, which means that values that should not have been removed have actually been removed for some reason. That is why the average, variance and other stats of elasticities calculated by that method cannot be called accurate values, either.

FIG. 4(c) is a histogram representing elasticities that were measured by the method disclosed in Patent Document No. 4. Almost all of those unrealistic elasticities have been removed but the vascular wall data that should not have been removed has also been removed by mistake. That is why this distribution does not include the elasticity value of the entire vascular wall, and therefore, the average, variance and other stats of elasticities calculated by that method cannot be called accurate ones, either.

FIG. 4(d) is a histogram representing the subject's elasticity values that were obtained by the method of this preferred embodiment. According to this preferred embodiment, the tracking waveform choosing section 107 excludes inappropriate position tracking waveforms and calculates the elasticity value based on only appropriate position tracking waveforms. Since the position tracking waveforms are chosen by their shape, for example, as described above, the measurement data can be selected more accurately and more properly than in the prior art in which data is excluded inappropriately based on only the elasticity values. As a result, in the histogram shown in FIG. 4(d), unrealistic elasticity values have been removed almost completely and yet appropriate elasticity values are included without missing anything. Consequently, the average, variance and other stats of the elasticities thus obtained become almost accurate ones. In this case, if the frequencies of occurrence are given weights according to the area of the elasticity value, the frequencies can be even more accurate values.

As described above, the ultrasonic diagnostic apparatus of the present invention chooses at least two position tracking waveforms, including the one associated with the boundary, from multiple position tracking waveforms by reference to at least one of the position tracking waveforms associated with the multiple measuring points, the location of the boundary, and the amplitudes of the received signals, and calculates the tissue attribute value using the position tracking waveform chosen. As a result, the measurement data can be selected more accurately and more appropriately than in the prior art, and accurate tissue attribute with no improper data can be obtained. On top of that, as the tissue attribute value is calculated using the position tracking waveform that is associated with the boundary, the tissue attribute value is never calculated over two different tissues. That is to say, an accurate tissue attribute value can be obtained for each tissue. Furthermore, the tissue attribute values can be obtained accurately over the entire region of interest without producing any missing parts either dispersively or just locally.

In the preferred embodiment described above, a subject, including the vascular wall to be displaced periodically, is supposed to be the object of measurement. However, the tissue attribute value of a subject including a resting organ could also be obtained. In that case, the subject is deformed intentionally by applying force to the subject periodically. For example, by pressing down the probe toward the subject periodically, strain may be generated in the subject and its tissue attribute value may be measured. The tracking waveform choosing section 107 chooses position tracking waveforms under the condition that the closer to the probe 101 a given measuring point is, the smaller the magnitude of displacement and the more distant from the probe 101 the measuring point is, the greater the magnitude of displacement is. More specifically, the tracking waveform choosing section 107 chooses the position tracking waveforms except any position tracking waveform associated with a measuring point, which is located relatively close to the probe 101 but at which the motion is more significant than at another measuring point that is located farther away from the probe 101. The constraint to be imposed changes according to the subject's shape, the point to which external pressure or vibration is applied periodically, and how such a pressure or vibration is applied. That is why by changing the conditions according to those parameters, the present invention can be applied. For example, if a low-frequency vibrator is arranged at a different position on the subject from the probe 101, the vibration will propagate from the low-frequency vibrator. By taking this fact into consideration, if there is any position tracking waveform at a measuring point that is located close to the low-frequency vibrator but at which vibrations start to be produced at a delayed timing, such a position tracking waveform may be excluded.

Furthermore, the tracking waveform choosing section 107 may take advantage of the feature of a position tracking waveform by reference to the function of the object. For example, if the subject's tissue is a vascular wall, the timings of shrinkage and dilation represented by the position tracking waveforms at respective measuring points are sequentially delayed from some central point to some peripheral point between multiple measuring points that are defined along the axis of the blood vessel. This is because blood with high pressure is supplied from a central point, i.e., from the heart. That is why position tracking waveforms that do not satisfy such a condition, e.g., a position tracking waveform associated with a measuring point that is located closer to the peripheral tissue but at which the timing of shrinkage or dilation is earlier than at the central point, may be excluded.

Also, as far as the heart is concerned, the timings of shrinkage are different between the inner cardiac muscle and the outer cardiac muscle. More specifically, in the systolic phase, the inner cardiac muscle starts to shrink first, and then the outer cardiac muscle starts to shrink. On the other hand, in the diastole phase, the outer cardiac muscle starts to dilate first, and then the inner cardiac muscle starts to dilate. That is why if the measuring points are set in the thickness direction of the cardiac muscle, position tracking waveforms that do not satisfy either the condition that the timings of shrinkage represented by the position tracking waveforms at respective measuring points are delayed sequentially from the inner cardiac muscle toward the outer one or the condition that the timings of dilation represented by the position tracking waveforms at respective measuring points are delayed sequentially from the outer cardiac muscle toward the inner one, may be excluded.

INDUSTRIAL APPLICABILITY

The present invention can be used effectively to make an ultrasonic diagnostic apparatus that obtains tissue attribute values.

The invention claimed is:

1. An ultrasonic diagnostic apparatus comprising:
   a transmitting section configured to drive a probe so that the probe sends out ultrasonic waves toward a subject one after another;
   a receiving section configured to get an echo, which has been produced as a result of reflection of each said ultrasonic wave from the subject, received by the probe, thereby generating a received signal;
   a tissue tracking section configured to generate position tracking waveforms, each of which represents the positional displacement of an associated one of first measuring points that have been set on the subject, based on the received signals;
   a boundary detecting section configured to determine the boundary location of the subject's tissue;
   a tracking waveform choosing section configured to choose at least two position tracking waveforms corresponding to at least two second measuring points selected from among the first measuring points, the at least two second measuring points including one of the first measuring points which is located on the boundary location determined by the boundary detecting section, and at least one other of the first measuring points;
   wherein the second measuring point that is the at least one other of the first measuring points differs from the first measuring point located on the boundary location, and differs from first measuring points for which the amplitude of the received signal and/or the position tracking waveform satisfies a predetermined condition; and
   a tissue attribute value calculating section configured to calculate a tissue attribute value of the subject between the at least two second measuring points using the position tracking waveforms that are associated with the at least two second measuring points.

2. The ultrasonic diagnostic apparatus of claim 1, wherein the position tracking waveform that satisfies the predetermined condition is a position tracking waveform with noise, a position tracking waveform representing a different displacement direction from the others, or a position tracking waveform with a different fundamental shape from the others.

3. The ultrasonic diagnostic apparatus of claim 2, wherein the tracking waveform choosing section determines the position tracking waveform that satisfies the predetermined condition by pattern matching, correlation coefficients, difference calculation or fast Fourier transform.

4. The ultrasonic diagnostic apparatus of claim 1, wherein the position tracking waveform that satisfies the predetermined condition is a position tracking waveform associated with the first measuring point where the amplitude of the received signal is greatest among the position tracking waveforms associated with two or more adjacent measuring points and being substantially identical with each other.

5. The ultrasonic diagnostic apparatus of claim 1, wherein the position tracking waveform that satisfies the predetermined condition is a position tracking waveform that does not satisfy a constraint imposed by the shape of the subject's tissue.

6. The ultrasonic diagnostic apparatus of claim 5, wherein the tissue has the shape of a cylinder, the measuring points are set in the radial direction of the cylinder, and the position tracking waveform that satisfies the predetermined condition is a position tracking waveform if the amplitudes of all the other position tracking waveforms associated with multiple measuring points, but that position tracking waveform, decrease from an inner point of the cylinder toward an outer point thereof.

7. The ultrasonic diagnostic apparatus of claim 1, wherein the position tracking waveform that satisfies the predetermined condition is a position tracking waveforms that do not satisfy a constraint imposed by a function of the subject's tissue.

8. The ultrasonic diagnostic apparatus of claim 7, wherein the tissue is a vascular wall, the measuring points are set in the axial direction of the vascular wall, and the position tracking waveform that satisfies the predetermined condition is a position tracking waveform if all the other position tracking waveforms associated with the multiple measuring points, but that position tracking waveform, represent timings of shrinkage and dilation that are delayed sequentially from some central point toward a peripheral point.

9. The ultrasonic diagnostic apparatus of claim 7, wherein the tissue is the heart, the measuring points are set in the thickness direction of its cardiac muscle, and the position tracking waveform that satisfies the predetermined condition is a position tracking waveform if all the other position tracking waveforms associated with the multiple measuring points, but that position tracking waveform, represent either timings of shrinkage that are delayed sequentially from some inner point on the cardiac muscle toward an outer point on the muscle or timings of dilation that are delayed sequentially from some outer point on the cardiac muscle toward an inner point on the muscle.

10. The ultrasonic diagnostic apparatus of claim 1, wherein the subject has been deformed under external force and the position tracking waveform that satisfies the predetermined condition is a position tracking waveforms that does not satisfy a constraint imposed by the point, direction, or method of applying the force.

11. The ultrasonic diagnostic apparatus of claim 10, wherein the external force is applied by pressing the probe down toward the subject, and the position tracking waveform that satisfies the predetermined condition is a position tracking waveform, of which the amplitude does not increase as the point of measurement is set at a greater distance from the probe.

12. The ultrasonic diagnostic apparatus of claim 1, further comprising a user interface that allows the user to specify the boundary location,
   wherein the boundary detecting section determines the location that has been specified by the user to be the boundary.

13. The ultrasonic diagnostic apparatus of claim 1, wherein the boundary detecting section is connected to an external modality and gets boundary information from the modality.

14. The ultrasonic diagnostic apparatus of claim 1, wherein the tracking waveform choosing section chooses a position tracking waveform that is associated with a measuring point on the tissue with respect to the boundary detected by the boundary detecting section.

15. The ultrasonic diagnostic apparatus of claim 1, further comprising a display section to display the tissue attribute values.

16. The ultrasonic diagnostic apparatus of claim 15, wherein the display section displays the tissue attribute values as a two-dimensional distribution image.

17. The ultrasonic diagnostic apparatus of claim 16, wherein the display section displays a histogram of the tissue attribute values.

\* \* \* \* \*

UNITED STATES PATENT AND TRADEMARK OFFICE
CERTIFICATE OF CORRECTION

PATENT NO. : 8,469,889 B2  
APPLICATION NO. : 12/933129  
DATED : June 25, 2013  
INVENTOR(S) : Takao Suzuki and Takenori Fukumoto Page 1 of 1

It is certified that error appears in the above-identified patent and that said Letters Patent is hereby corrected as shown below:

On the Title Page the following should appear:
Item (30) Foreign Application Priority Data
March 27, 2008     (JP) 2008-082816

Signed and Sealed this
Thirty-first Day of December, 2013

Margaret A. Focarino
*Commissioner for Patents of the United States Patent and Trademark Office*